United States Patent [19]

Nagarajan et al.

[11] Patent Number: 4,801,537
[45] Date of Patent: Jan. 31, 1989

[54] VECTOR FOR EXPRESSION OF POLYPEPTIDES IN BACILLI

[75] Inventors: Vasantha Nagarajan, Rockville, Md.; Craig S. Rhodes, Washington, D.C.; Carl D. B. Banner, Bethesda, Md.

[73] Assignee: Genex Corporation, Gaithersburg, Md.

[21] Appl. No.: 717,800

[22] Filed: Mar. 29, 1985

Related U.S. Application Data

[63] Continuation-in-part of Ser. No. 618,902, Jun. 8, 1984, abandoned, which is a continuation-in-part of Ser. No. 511,198, Jul. 6, 1983, abandoned.

[51] Int. Cl.$^4$ .................... C12P 21/00; C12N 15/00; C12N 9/54; C12N 1/20
[52] U.S. Cl. .................................. 435/68; 435/172.3; 435/221; 435/320; 435/839; 435/252.31; 935/29; 935/48; 935/74
[58] Field of Search .................. 435/172.3, 68, 317; 935/22, 10, 24, 74

[56] References Cited

U.S. PATENT DOCUMENTS 4,411,994  10/1983  Gilbert et al. .................... 435/71

FOREIGN PATENT DOCUMENTS

| | | |
|---|---|---|
| 0032238 | 7/1981 | European Pat. Off. . |
| 0073029 | 3/1983 | European Pat. Off. . |
| 0077109 | 4/1983 | European Pat. Off. . |
| 0151760 | 8/1983 | European Pat. Off. . |
| 0134048 | 3/1985 | European Pat. Off. . |
| 0149241 | 7/1985 | European Pat. Off. . |
| 0130756 | 9/1985 | European Pat. Off. . |
| 8400773 | 3/1984 | PCT Int'l Appl. . |
| 091268  | 7/1982 | United Kingdom . |

OTHER PUBLICATIONS

Takagi et al., *J. Bacteriol.* 163(3): 824 831 (1985).
Wong et al., *P.N.A.S. U.S.A.* 81: 1184–1188 (1984).
Vasantha et al., *Chem. Ab.* 102(23): 16, Abstract No. 198918w (1985).
Wells et al., *Chem. Ab.* 102(23): 16, Abstract No. 198919x (1985).
Vasantha et al., *Chem. Ab.* 102(3): 152, Abstract No. 18497b (1985).
Research Dev. Corp. of Japan, *Chem. Ab.* 100(5): 352, Abstract No. 33279j (1984).
Kogyo Gijutsuin, *Patents Abstracts of Japan* 8(156): (C-234) [1953] (1984).
Hussain et al., *Agricultural and Biological Chem.* 46(1): 65–74 (1982).
Kogyo Gijutsuin, *Patents Abstracts of Japan* 9(301): (c-316) [2024] (1985).
Agency of Industrial Sciences and Technology, *Chem. Ab.* 103(5): 116, Abstract No. 33022g (1985).
Markland et al., *J. Biol. Chem.* 242: 5198–5211 (1967).
Welker et al., *J. Bacteriol.* 94: 1124–1130 (1967).
Power et al., *PNAS U.S.A.* 83: 3096–3100 (1986).
Wells et al., *Nucl. Acids Res.,* 11:7911–7925 (1983).
Lofdahl et al., *Proc. Natl. Acad. Sci. U.S.A.,* 80:697–701 (1983).
Talmadge et al., *Proc. Natl. Acad. Sci. U.S.A.,* 77:3369–3379 (1980).
Palva et al., *Gene,* 19:81–87 (1982).
Palva et al., *Proc. Natl. Acad. Sci. U.S.A.,* 79:5582–5586 (1982).
Fujii et al., *J. Bact.,* 154:831–837 (1983).
Gryczan et al., *Mol. gen. Genet.,* 177:459–467 (1980).
Welker and Campbell, *J. Bact.,* 94:1124–1130 (1967).
Nagarajan et al., *J. Bact.,* 159:811–819 (Sep. 1984).

*Primary Examiner*—Thomas G. Wiseman
*Assistant Examiner*—Thomas D. Mays
*Attorney, Agent, or Firm*—Saidman, Sterne, Kessler & Goldstein

[57] ABSTRACT

A replicable plasmidic expression vector, capable of high levels of expression and secretion of polypeptides in a bacillus is disclosed. The vector contains a DNA sequence comprising the promoter and regulatory regions which control expression and secretion of proteases in a bacillus operably liked to a DNA sequence encoding the amino acid sequence of a polypeptide. The expression vector is particularly useful in the production of *B. amyloliquefaciens* proteases or other heterologous proteins in *B. subtilis*.

47 Claims, 8 Drawing Sheets

```
TTTTCCGCAATTATATCATTGACATATCAATCATGATATTCATTATTTTATAAATGGTTTCACAGCTTTTCTCCGTCAAGAAGCCA        100
AAGACTGATTTCCGCTTACGTTCCATCGTCTCTGTATTCAACAGTCTCTGTATTCAACAAAAGATGACATTTACCTGTTTTGGAACAACCCCAAAATGGAAACAAACCGT  200
TCGACCCAGGAAACAAGCGAGTGATTGCTCCTGTGTACATTTACTCATGTCCATCCATCGGTTTTTCCATTAAATTTAAATATTTCGAGTTCCTACGA  300
AACGAAGAGAGATGATATACCTAAATAGAAATAAACAATCTGAAAAAAATTGGGTCTACTAAAATATTATTCCATACTATACAATTAATACACAGAAT  400
                                                -107             -100
AATCTGTCTATTGGTTATTCTGCAAATGAAAAAAAGGAGAGGATAAAGA  GTG AGA GGC AAA AAA GTA TGG ATC AGT TTG CTG TTT  485
                                                 fmet Arg Gly Lys Lys Val Trp Ile Ser Leu Leu Phe
                                                                                      PRO
GCT TTA GCG TTA ATC TTT ACG ATG GCG TTC GGC AGC ACA TCC TCT GCC CAG GCG GCA GGG AAA TCA AAC GGG GAA  560
Ala Leu Ala Leu Ile Phe Thr Met Ala Phe Gly Ser Thr Ser Ser Ala Gln Ala Ala Gly Lys Ser Asn Gly Glu
                                                                              -50
AAG AAA TAT ATT GTC GGG TTT AAA CAG ACA ATG AGC ACG ATG AGC TTT AAG GCT GCT AAG AAA GAT GTC ATT TCT GAA  635
Lys Lys Tyr Ile Val Gly Phe Lys Gln Thr Met Ser Thr Met Ser Ala Ala Lys Lys Asp Val Ile Ser Glu AAA GGC GGG AAA GTG CAA AAG CAA TTC AAA TAT GTA GAC GCA GCT TCA GCT ACA TTA AAC GAA AAA GCT GTA AAA  710
Lys Gly Gly Lys Val Gln Lys Gln Phe Lys Tyr Val Asp Ala Ala Ser Ala Thr Leu Asn Glu Lys Ala Val Lys
                                                                                Mature
GAA TTG AAA AAA GAC GCC AGC GTC GCT TAC GTT GAA GAA GAT CAC GTA GCA CAT GCG TAC GCG CAG TCC GTG CCT  785
Glu Leu Lys Lys Asp Ser Val Ala Tyr Val Glu Glu Asp His Val Ala His Ala Tyr Ala Gln Ser Val Pro TAC GGC GTA TCA CAA ATT AAA GCC CCT GCT CTG CAC TCT CAA GGC TAC ACT GGA TCA AAT GTT AAA GTA GCG GTT  860
Tyr Gly Val Ser Gln Ile Lys Ala Pro Ala Leu His Ser Gln Gly Tyr Thr Gly Ser Asn Val Lys Val Ala Val
    ClaI
                                                                     50
ATC GAC AGC GGT ATC GAT TCT TCT CAT CCT GAT TTA AAG GTA GCA GGC GGA GCC ATG AGC GTT CCT TCT GAA ACA  935
Ile Asp Ser Gly Ile Asp Ser Ser His Pro Asp Leu Lys Val Ala Gly Gly Ala Ser Met Val Pro Ser Glu Thr AAT CCT TTC CAA GAC AAC AAC TCT CAC TCT CAC GGA ACT CAC GTT GCC GGC ACA GTT GCG GCT CTT AAT AAC TCA ATC GGT  1010
Asn Pro Phe Gln Asp Asn Asn Ser His Gly Thr His Val Ala Gly Thr Val Ala Ala Leu Asn Asn Ser Ile Gly
 *   *                                  *
                                                                         100
GTA TTA GGC GTT GCG CCA AGC GCA TCA CTT TAC GCT GTA AAA GTT CTC GGT GCT GAC GGT TCC GGC CAA TAC AGC  1085
Val Leu Gly Val Ala Pro Ser Ala Ser Leu Tyr Ala Val Lys Val Leu Gly Ala Asp Gly Ser Gly Gln Tyr Ser
 *   *                      *                                       *   *
```

VECTOR FOR EXPRESSION OF POLYPEPTIDES IN BACILLI

BACKGROUND OF THE INVENTION

This invention relates to the construction, isolation and identification of plasmids which contain DNA sequences directing the expression and secretion of specific classes of proteases and which facilely transform microorganisms to hyperproduce and secrete the specified proteases or other proteins.

Proteases are a group of enzymes which hydrolyze the peptide bonds of proteins. Proteases which are produced by bacteria can be classed in two general types. Those which are active at neutral pH and usually require a cofactor, such as zinc, to be active are called neutral proteases and can be inactivated by chelating agents such as ethylenediaminetetraacetic acid (EDTA) which remove the cofactor from the enzyme. Those which are active at high pH and cleave peptide bonds by a process analogous to alkaline hydrolysis are termed alkaline proteases. Alkaline proteases are also referred to as subtilisin and serine protease. Alkaline proteases can be inactivated by chemicals such as phenylmethylsulfonyl fluoride (PMSF) or by diisopropyl fluorophosphate (DFP). Bacterial proteases are available commercially from a number of suppliers (OPD Chemical Buyers Directory, A. P. Kavaler, ed, Schnell Publishing Co., Inc. New York, N.Y. 1982) and are used industrially to clarify beer, tan leather, tenderize meat, curdle milk and in the formulation of specialized detergents. Bacterial enzymes are extracted from cultures of specific strains of microorganisms, many of which are the result of careful selction and of artificial mutation (e.g. UV irradiation). Limitations on the production of enzymes include the rate at which the microorganism produces the enzyme, the degree to which the microorganism excretes the enzyme produced, and the stability of the microorganism in culture.

In recent years, processes have been developed for inserting into a bacterial organism a gene or genes from another organism so that the bacterium will produce "foreign" proteins. The technique for introducing the DNA which directs ("codes for") the production of an enzyme involves the cleavage of DNA from the source cell using one of a number of "restriction endonucleases", attaching ("ligating") the cleaved DNA to DNA from a plasmid to form a "vector," and introducing the vector into the host under conditions which make the "transformation" successful.

The organisms of the genus Bacillus are aerobes and have been widely used in the fermentation industry because they are non-pathogenic and, in the case of protein production, because they have the ability to secrete proteins. Most research into recombinant DNA has been performed using *E. coli* as the host. *E. coli* is generally a non-secreting microorganism well-developed for the cloning of recombinant plasmids but not well suited for the commercial production of proteins. Bacillus species, particularly *B. subtilis*, cannot be transformed using monomer plasmid or conventional techniques developed for E. coli. (Canosi et al. *Mol. gen. Genet.*, 166:259 [1978], Keggins et al., *Proc. Nat. Acad. Sci. U.S.*, 75:1423 [1978] and Michel et al., *Gene*, 12:147 [1978]). A number of alternative strategies have been developed for the transformation of *B. subtilis*, including the use of plasmid multimers (Canosi), the use of polyethylene glycol to induce DNA uptake in protoplasts (Chang S. and Cohen S.N., *Mol. gen. Genet.*, 168:111 [1979]) and the use of the marker rescue technique (Gryczan et al., *Mol. gen. Genet.*, 177:459 [1980]). A structural gene for alpha-amylase, including the associated control regions, from *B. amyloliquefaciens* has been shotgun cloned into *B. subtilis*. The alpha-amylase was expressed in *B. subtilis* at a rate five times that produced by the source *B. amyloliquefaciens* (Palva I. Gene, 19:81-87 [1982]).

A Bacillus transformant, e.g. a *B. subtilis* transformant, expressing large amounts of proteases would have particular commercial importance. Moreover, an efficient expression vector for transforming *B. subtilis* which includes a promoter, operator and ribosome binding site, as well as the structural gene for a specific enzyme such as a protease would be useful not only because it could be used to transform *B. subtilis* to produce the enzyme, but also because it could provide an efficient promoter and regulatory region which could be used for the expression and secretion of heterologous proteins in *B. subtilis*.

SUMMARY OF THE INVENTION

The present invention is based upon applicant's discovery that the genetic information which serves to regulate the expression of proteases in a first bacillus species such as *B. amyloliquefaciens* can be incorporated into a second bacillus species such as *B. subtilis* in the form of a replicable plasmidic expression vector to produce a transformant microorganism which is capable of high levels of expression and secretion of the protease or, if desired, other heterologous polypeptides, i.e., polypeptides not naturally produced by the bacillus host.

Accordingly, there is provided by the present invention a replicable plasmidic expression vector capable of directing high level expression and secretion of a polypeptide in a transformed bacillus, such as *B. subtilis*, which comprises:

(a) a replicon;

(b) a DNA sequence comprising the promoter and regulatory regions which control expression and secretion of a bacillus protease, such as a *B. amyloliquefaciens* protease; and (c) a DNA sequence encoding the amino acid sequence of a polypeptide, operably linked to said promoter and regulatory region.

In one embodiment of the invention, the polypeptide which is encoded is the protease whose expression and secretion in its cell of origin is controlled by the particular promoter and regulatory regions, for example, the promoter and regulatory regions for the alkaline protease or neutral protease genes of *B. amyloliquefaciens*.

In another embodiment, the polypeptide which is encoded is a heterologous polypeptide which is not normally under the control of the protease promoter and regulatory region. The heterologous polypeptide can be a prokaryotic protein, e.g., protein A, or it can be a eukaryotic protein, e.g., prorennin.

There are also provided, in accordance with the invention, transformant microorganisms containing the previously mentioned replicable plasmidic expression vector; a method of producing a polypeptide by expression of the DNA encoding the polypeptide in the transformant microorganism; and a method of producing a microorganism for the expression of a protease enzyme which comprises transforming a bacillus, such as *B.*

*subtilis*, with the replicable plasmidic expression vector of the invention, preferably a vector in which the polypeptide which is encoded by the DNA sequence is a *B. amyloliquefaciens* protease.

Advantageously, there are provided, in accordance with the teachings of the invention, means for controlling expression of genes for heterologous polypeptides which are linked to the promoter and regulatory regions of bacillus protease genes. In one embodiment of the invention, a heterologous gene linked to the promoter and regulatory region of a neutral protease gene is expressed in a bacillus host during the exponential growth phase. In another embodiment, a heterologous gene linked to the promoter and regulatory region of an alkaline protease gene is expressed in a bacillus host after exponential growth has ceased.

BRIEF DESCRIPTION OF THE DRAWINGS

In FIG. 1, stippling denotes apr[BamP], ∿∿∿ indicates other *B. amyloliquefaciens* DNA, and—indicates pBD64 vector sequence. A detailed map of the insert indicating the location of several restriction sites and of apr[BamP](→) is shown beneath the plasmid.

In FIG. 2, stippling denotes npr[BamP], ∿∿∿ indicates other *B. amyloliquefaciens* DNA, and—indicates pBD64 vector sequence. A detailed restriction map of the insert, indicating the location of several restriction sites and of npr[BamP] (→) is shown beneath the plasmid.

FIG. 3 depicts the nucleotide sequence of the apr[BamP] gene and the encoded amino acid sequence of alkaline protease (subtilisin) produced by *B. amyloliquefaciens*. Both strands were sequenced from several independent overlapping clones. The putative ribosome binding site and the transcriptional terminator have been underlined. The previously published amino acid sequences (Smith et al., *J. Biol. Chem.*, 214:5974–5976 [1966]) at the regions of mismatch (indicated in FIG. 3 by asterisks) are: 56,57(Pro,Asn); 61(Asp); 88,89(Ser,Ala); 98,99(Asp,Ala); 158,159(Ser,Thr); 251(Gln).

FIG. 4 depicts the nucleotide sequence of the npr[BamP] gene and the encoded amino acid sequence of neutral protease produced by *B. amyloliquefaciens*. Both strands were sequenced from several independent overlapping clones. The putative ribosome binding site and the transcriptional terminator have been underlined. The N-terminus of the mature protein has been identified based on perfect homology to the N-terminal sequence of neutral protease A from *B. subtilis* NRRL B3411 (Levy et al., Proc. Nat'l. Acad. Sci., U.S.A., 72:4341–4345 [1975]).

FIG. 7 is a plot of cell density and protease activity vs. time of fermentation for B. subtilis strain GX2821, carrying the apr[BamP] gene or a multicopy plasmid. The arrow denotes the end of exponential growth.

FIG. 8 is a plot of cell density and protease activity vs. time of fermentation for B. subtilis strain GX2842, carrying the npr[BamP] gene on a multicopy plasmid. The arrow denotes the end of exponential growth.

DETAILED DESCRIPTION OF THE INVENTION

The replicable plasmidic expression vector of the invention is produced, using techniques of DNA recombination, by inserting a DNA sequence described hereinafter into a plasmid which is capable of transforming and replicating in a host microorganism. (Unless otherwise indicated, all DNA referred to herein is in the form of double stranded DNA.) A plasmid is a non-chromosomal loop of double stranded DNA found, often in multiple copies per cell, in microorganisms. The plasmid contains within its DNA sequence the genetic information necessary for replicating itself (i.e. a "replicon"). Additionally, many plasmids contain sequences of DNA which encode a phenotypic trait, such as resistance to specific antibiotics, which is useful when one desires to screen for the presence of the particular plasmid.

Any plasmid which is capable of transforming and replicating itself in the host microorganism can be employed in the practice of this invention. When the host microorganism is *B. subtilis*, we prefer to employ the plasmid pBD64 to prepare the replicable plasmidic expression vector and to use, as the host, a *B. subtilis* containing the homologous plasmid pUB110. Both plasmids are described in Gryczan et al., supra. An homologous plasmid is a resident plasmid in *B. subtilis* which has a large region of DNA sequence homology with the exogenous plasmid which one desires to introduce and which is capable of recombining with the exogenous plasmid during transformation. The resident plasmid pUB110 is an homologous plasmid for pBD64. The use of a resident homologous plasmid to increase the efficiency of transformation—which we employed in practicing the invention—is described in the Gryczan et al. paper and is known as the marker rescue transformaton technique.

The DNA sequence which is inserted into the plasmid to produce the replicable plasmidic expression vector of the invention contains a DNA sequence comprising the promoter and regulatory regions which control expression and secretion of a protease in a first bacillus organism, preferably *B. amyloliquefaciens*, operably linked to a DNA sequence encoding the amino acid sequence of a polypeptide. In one embodiment, the encoded polypeptide is a *B. amyloliquefaciens* protease (alkaline or neutral).

The promoter is a sequence of deoxyribonucleotides which is recognized and bound by the enzyme RNA polymerase and may be overlapped by the so-called operator sequence. The operator sequence is recognized and bound by a repressor protein, which is not present or is inactive under conditions of expression. The RNA polymerase binds to the promoter and then travels along the coding strand of the DNA (provided it is not blocked by a bound repressor protein) transcribing the sequence of bases into corresponding mRNA. A portion of the DNA which is transcribed encodes a ribosome binding site, known as the Shine-Dalgarno sequence. This is followed by a translation initiation signal, normally ATG in the DNA sequence, which is the nucleotide triplet encoding the first amino acid in the structural gene. The rest of the transcript encodes the structural gene of a polypeptide. RNA polymerase action ceases when it encounters a termination signal in the DNA. The resulting mRNA can be effectively translated at the ribosome to produce the desired protein. In the case of secreted proteins, such as α-amylase and proteases, in addition to the promoter, operator and ribosome binding site there is also a "signal sequence" following the translation initiation signal. This encodes a polypeptide of about 15 to 30 amino acids in length that usually contains a positively charged amino terminal domain followed by a hydrophobic domain. The signal sequence, which precedes the amino acid sequence of the mature protein, is necessary for secretion of proteins across the cell membranes and is removed from the secreted protein during or immediately after translocation across the cell membrane.

The promoter, operator, ribosome binding site and translation initiation sequences serve to control the efficiency of expression of the protein. As used herein, the term "promoter and regulatory regions" refers to the DNA sequence containing the bases encoding the promoter, operator, ribosome binding site and translation intitiation signal, as well as the secretion signal sequence.

The DNA sequence (promoter and regulatory region) which is incorporated into the replicable plasmidic expression vector of the invention preferably is one which controls the expression and secretion of a protease in *B. amyloliquefaciens* and, therefore, can be obtained from *B. amyloliquefaciens*. In one embodiment of the invention, the structural gene which is operably linked to the promoter and regulatory regions (including the signal sequence) is one which encodes the amino acid sequence of the protease whose expression and secretion is controlled by the particular promoter and regulatory sequence in *B. amyloliquefaciens*. It will be appreciated, however, that DNA sequences encoding other useful heterologous polypeptides can be operably linked to the promoter and regulatory regions derived from *B. amyloliquefaciens*, using known techniques of in vitro DNA recombination, and inserted into a plasmid to produce a replicable plasmidic expression vector which can be employed to direct expression and secretion of the heterologous polypeptide in *B. subtilis*. As merely exemplary of such useful polypeptides one can mention eukaryotic polypeptides such as human interferons, insulin, human and animal growth hormones, prorennin and the like, and prokaryotic polypeptides such as protein A. These are examples of polypeptides having known amino acid sequences which have been expressed by recombinant DNA techniques in *E. coli*. An efficient means of expressing these polypeptides in *B. subtilis* such as the method of our invention offers distinct advantages over expression in *E. coli*, for example, secretion of the polypeptide from the organism, which simplifies purification and increases yield, and elimination of the danger of contamination of the product by *E. coli* endotoxins.

The DNA sequence encoding the promoter and regulatory regions and, if desired, the DNA sequence encoding the *B. amyloliquefaciens* protease can be obtained by direct cleavage of a segment containing the desired sequence from chromosomal DNA of *B. amyloliquefaciens*.

Alternatively, one could isolate the mRNA from *B. amyloliquefaciens* which is transcribed from the desired DNA sequence and use the mRNA as a template to produce cDNA in the presence of reverse transcriptase. The cDNA can then be employed to isolate the desired promoter, regulatory regions and structural gene.

The chromosomal DNA or the cDNA can be inserted into a cloning vector which can be used to transform a host microorganism. The transformant is then grown up to produce a large population of clones containing the desired DNA sequence.

In order to insert the Bacillus DNA, e.g. the *B. amyloliquefaciens* DNA into the plasmid, it is necessary that the DNA have ends which are complementary to the ends generated at an endonuclease cleavage site on the plasmid conveniently located for expression. This can be achieved by digesting, either completely or partially, the ends of the DNA segment from *B. amyloliquefaciens* with a restriction endonuclease corresponding to the desired insertion site on the plasmid. The DNA sequences encoding the promoter and regulatory regions and the amino acid sequence of the polypeptide are inserted into the plasmid (which has been linearized by cleavage with an appropriate restriction endonuclease) by reacting in the presence of a ligating enzyme such as T4 DNA ligase.

The resulting recombinant plasmids are used to transform the host bacillus microorganism, which can be screened for the presence of the expression vector having the desired DNA sequence in the appropriate orientation for expression. Transformation can be effected using known techniques (Contente, S. and Dubnau, D., *Plasmid*, 2:555-571(1979) and Chang & Cohen, supra).

The transformants can be screened for the presence of the desired recombinant plasmid by assaying for the presence of the activity characteristic of the polypeptide encoded by the DNA sequence. In the case of the DNA sequence encoding a *B. amyloliquefaciens* protease, the presence of the desired recombinant can be determined by the ability of the transformant cells to clear skim milk in agar.

If desired, the replicable plasmidic expression vector can be removed from the screened transformant by known techniques, such as the boiling preparation method, and used to transform other host bacillus microorganisms or one can employ the screened transformant directly to express the polypeptide. In the event one wishes to express the polypeptide in *E. coli*, it is preferred to employ a "shuttle vector," which can be prepared by cleaving and recombining the replicable plasmidic expression vector with a plasmid which is capable of efficient replication in *E. coli*, e.g., the plasmid pBR322.

Since *E. coli* is an excellent host for cloning, one may desire to prepare a shuttle vector from the replicable plasmidic expression vector for the purpose of replicating it in *E. coli*. The cloned vector can then be isolated from the *E. coli*, and the replicable plasmidic expression vector can be recovered therefrom by cleavage and recircularization and used to retransform *B. subtilis* or another host for expression.

The replicable plasmidic expression vector of the invention can be used to transform stage zero sporulation mutants of *B. subtilis*. The use of stage zero sporulation mutants of *B. subtilis* in fermentations offers the theoretical advantage of better control of contamination of the environment. Existing stage zero sporulation strains produce very low levels of protease. The plasmids produced and isolated by the above-described procedure are readily introduced into stage zero sporulation mutants of B. subtilis using the protoplast transformation method used to transform other strains of B. subtilis. The transformed stage zero sporulation B. subtilis produced the specified proteases at rates qualitatively indistinguishable from other transformed B. subtilis. The cells retain their characteristic failure to produce spores.

The polypeptide encoded by the DNA sequence in the replicable plasmidic expression vector can be produced by growing up the transformed microorganism under known fermentation conditions until a desired cell density is achieved and subjecting the transformants to conditions which initiate expression. Addition of inexpensive carbon sources such as soy protein, fish meal or any denatured protein that is available and economical may enhance expression.

The expressed polypeptide is then recovered from the other proteins and contaminants in the fermentation broth and purified using known techniques such as size exclusion chromatography, immunoaffinity chromatography and the like.

In one embodiment of the invention, a replicable plasmidic expression vector encoding B. amyloliquefaciens protease can be produced and used to transform B. subtilis in the following manner.

Cellular DNA from B. amyloliquefaciens is isolated using standard techniques and partially digested with a restriction endonuclease such as MboI under very mild conditions. It is then ligated to a vector, e.g., to the BamHI site of pBD64 which has ends complementary to those left by the MboI digestion. In the preferred embodiment, the B. amyloliquefaciens DNA was partially digested with MboI and ligated to the BamHI site of pBD64, which has markers for chloramphenicol and kanamycin resistance. An homologous plasmid to pBD64 is pUB110. (Other combinations of homologous plasmids and appropriate restriction endonucleases are suitable, provided that any cleavage sites in the B. amyloliquefaciens DNA within the desired insert are not cut.)

Transformed cells expressing protease are identified by growing the cells on agar containing skim milk. Colonies which produce zones of clearing of the milk are streaked for single colonies which clear milk at a greater rate than control colonies of B. subtilis and the desired colonies are easily selected and grown in shaker flasks. When the plasmid markers are for antibiotic resistance, the antibiotic may be added to the growth medium to select against colonies not carrying the plasmid. When pBD64 is used as the plasmid, chloramphenicol is the preferred antibiotic. Clones exhibiting the selection characteristic are grown for further analysis. Plasmids containing the genes for protease expression are isolated from cell cultures by standard techniques, such as the boiling preparation method (Holmes, D. S. and M. Quigley, Anal. Biochem., 114–193 [1981]). The isolated plasmids will readily retransform B. subtilis to express both the protease and the selected markers (i.e. antibiotic resistance). Alternatively, the isolated plasmids may be cloned in a host such as E. coli after being cleaved and ligated to a suitble vector for the transformation of E. coli such as the previously mentioned shuttle vector. When such a shuttle vector is produced, the ligated fragments may orient in either direction and it is desirable to screen the cloned plasmids at some point to select out the nonfunctional orientations.

B. amyloliquefaciens contains structural genes encoding both neutral and alkaline protease. B. subtilis transformed as described above will express either protease type, depending upon the particular structural gene incorporated into the replicable plasmidic expression vector. When vectors encoding the production of B. amyloliquefaciens protease were prepared in this manner, two different plasmids encoding alkaline protease and one plasmid for neutral protease were isolated. On the basis of restriction mapping of the isolated plasmids, the difference between the two alkaline protease plasmids appears to be the inclusion of an additional untranslated six hundred base pair sequence at the 3' end of the structural gene encoding the protease. No other functional or chemical differences are apparent and both proteins were approximately equal in activity. It is to be expected that minor, non-functional differences in plasmids and proteases may be obtained when this technique is used to produce the replicable plasmidic expression vectors and transformant microorganisms.

The replicable plasmidic expression vectors produced as described herein were compared for their ability to direct the hyperproduction of protease in B. subtilis. The rate of production was compared to that of B. subtilis transformed with the original plasmid pBD64 and with the B. amyloliquefaciens strain from which the DNA inserts were obtained. The rate of digestion of a dye-protein complex such as hide powder azure provides a convenient method for comparison. Under identical conditions, B. subtilis strains transformed with the plasmids containing the DNA insert from B. amyloliquefaciens were 150 to 200 times more productive of proteases than B. subtilis transformed with pBD64, and 1.5 to 2 fold more productive than B. amyloliquefaciens. Neutral protease producing cultures were marginally more productive than alkaline protease producing transformants in this test.

In another embodiment of the invention, a replicable plasmidic expression vector is constructed in which a heterologous structural gene encoding a polypeptide other than a B. amyloliquefaciens protease is placed under the control of the promoter and regulatory region of the alkaline protease (apr[BamP]) or neutral protease (npr[BamP]) gene from B. amyloliquefaciens. The expression vector is used to transform B. subtilis, in which it directs expression and secretion of the heterologous protein.

We have isolated and sequenced both apr[BamP] and npr[BamP]. The DNA sequences and inferred amino acid sequences of alkaline protease and neutral protease from B. amyloliquefaciens are respectively illustrated in FIG. 3 and FIG. 4. In both cases, DNA sequencing indicated a large open reading frame preceding the sequence encoding the mature protease. The inferred amino acid sequence of each gene contained a signal sequence and an additional polypeptide sequence ("pro" sequence) preceding the mature protein. We have identified the start point of translation as amino acid residue -107 for apr[BamP] and -221 for npr[BamP]. To demonstrate that the start point of translation of apr[BamP] in vivo is codon -107, codon -103 (AAA) was changed to an ochre (TAA) by site directed mutagenesis (Zoller and Smith, Nuc. Acids Res., 10:6487-6500 [1982]). Alkaline protease was produced from this ochre mutant derivative of apr[BamP] only when the host strain was $Su^+$.

An expression vector of the invention capable of directing expression and secretion of a heterologous polypeptide in *B. subtilis* can be constructed by inserting the structural gene for the heterologous protein into apr[BamP] or npr[BamP] downstream from and in phase with the coding sequence of the signal peptide. The hybrid DNA coding for the signal peptide of the *B. amyloliquefaciens* protease fused to the heterologous polypeptide, on an appropriate plasmid, is used to transform *B. subtilis*. A fusion protein comprising the signal peptide and the heterologous polypeptide will be expressed and secreted from the *B. subtilis*, with attendant cleavage of the signal peptide to release the heterologous polypeptide into the surrounding medium. If any portion of the sequence of apr[BamP] or npr[BamP] coding for the "pro" region of the protease is left intact upstream from the gene coding for the heterologous polypeptide, then that encoded portion of the "pro" region will remain fused to the N-terminus of the secreted polypeptide. Since "pro" regions have previously been associated only with eukaryotic proteases, it was somewhat surprising to find pro-coding regions in apr[BamP] and npr[BamP]. Moreover, the possible role of the "pro" region in facilitating secretion or protecting the protein from degradation during secretion was uncertain. Consequently, it was an unpredictable finding that secretion of the expression product of a heterologous gene linked directly to the signal coding sequence of apr[BamP] or npr[BamP], i.e., without the "pro" region, could be effected in *B. subtilis*. The putative signal processing site between the pre and pro regions has been identified based on a consensus "signal sequence" as outlined by Perlman and Halvorson (J. Mol. Biol., 167:391-409 1983]). The signal processing site can be determined by sequencing the amino terminus of the secreted protein. If the signal processing is found upstream or downstream of the proposed signal, heterologous fusions can be accordingly modified.

Insertion of the structural gene for the heterologous polypeptide downstream from the signal peptide coding region is advantageously effected by employing oligonucleotide-directed mutagenesis (Norris et al., *Nuc. Acids Res.*, 11:5103-5112 [1983]) of apr[BamP] or npr[BamP] to create an endonuclease cleavage site just downstream from the signal peptide coding region which is compatible with a cleavage site on the gene for the desired heterologous polypeptide. For example, we created a BamHI cleavage site just downstream from the signal coding sequence of apr[BamP] by the insertion of six deoxyribonucleotides after the fifth deoxyribonucleotide of the pro-coding region as follows:

The mutated apr[BamP] gene was cleaved at the BamHI site and ligated to a compatible BclI site 22 codons into the structural gene for protein A from *S. aureus* to create a fused gene coding for the signal peptide and first two amino acids of the pro region of alkaline protease (coded by GCA GGG) followed by the protein A sequence beginning with amino acid 23. A plasmid containing this fused gene was used to transform *B. subtilis*. Transformants containing the plasmid were grown and were found to secrete a protein which was shown by enzyme-linked immunosorbent assay and immunoblot analysis to correspond immunologically to protein A.

Genes for other heterologous polypeptides can be inserted into apr[BamP] or npr[BamP] and used to secrete the desired polypeptide from *B. subtilis* in a manner analogous to that which we employed with the protein A gene.

Analysis of the expression of apr[BamP] and npr[BamP] on multicopy plasmids in *B. subtilis* in either synthetic or complex media revealed that they are each regulated differently. Under these conditions, the rate of neutral protease accumulation is maximal during exponential growth. In contrast, the rate of alkaline protease accumulation is maximal after the end of exponential growth. This was a somewhat surprising finding, since it has generally been believed that both neutral protease and alkaline protease are produced after exponential growth when the Bacilli are in the stationary phase, (see, e.g., Yang, M. Y. et al., J. Bact., 160, p. 15-21 [1984]).

The discovery that npr[BamP] and apr[BamP] are differently regulated provides a convenient means for controlling the expression of heterologous genes which are placed under the control of the promoter and regulatory region of a protease gene in a Bacillus host. In continuous fermentation processes nutrients are continuously replenished in the medium so that the microorganisms are effectively in a continous growth phase. By contrast, in a non-continuous fermentation process nutrients are provided to the medium at the beginning of the fermentation. Eventually, one or more nutrients become depleted in the medium, causing the microorganisms to enter a stationary phase. The selection of a continuous or noncontinuous fermentation process is largely a matter of process economics, as will be understood by those skilled in the art.

In the case of production of a heterologous protein in a continuous fermentation process, one would desire to employ an expression system which maximizes expression of the protein during the growth phase. Accordingly, one embodiment of the invention provides a method for producing a polypeptide which comprises transforming a Bacillus strain with a plasmid comprising a replicon, a DNA sequence comprising the promoter and regulatory regions of a gene for neutral protease and a DNA sequence encoding the amino acid sequence of a heterologous polypeptide operably linked to the promoter and regulatory region of the neutral protease gene; growing the transformed bacilli in a culture medium; and expressing the heterologous polypeptide during exponential growth of the bacilli.

There may also be instances in which one desires to limit the bulk of expression of the heterologous polypeptide to the post-exponential growth phase, for example, when the heterologous polypeptide is toxic to the cells or substantially inhibits cell growth. Accordingly, another embodiment of the invention provides a method for producing a polypeptide which comprises transforming a Bacillus strain with a plasmid comprising a replicon, a DNA sequence comprising the promoter and regulatory regions of a gene for alkaline protease and a DNA sequence encoding the amino acid sequence of a heterologous protein operably linked to the promoter and regulatory region of the alkaline protease gene; growing the transformed bacilli in a culture medium; and expressing the heterologous polypeptide after exponential growth of the bacilli has ceased.

The invention will be further illustrated by the following examples:

EXAMPLE I

Construction of a Replicable Plasmidic Expression Vector Containing a Structural Gene For Protease and Transformation of B. subtilis Bacillus amyloliquefaciens (ATCC 23844) was isolated according to Saito, H. and Miura (Biochim. Biophys. Acta, 72:619 [1963]) and partially digested with MboI (Old, R. W. and Primrose, S. B., "Principles of Gene Manipulation", 2nd ed., Univ. of Calif. Press, Berkley, 1981). 250 μg of B. amyloliquefaciens chromosomal DNA was digested with 192 units of MboI for 7 min. at 37° C. The digestion was terminated by phenol:-chloroform extraction and the DNA was ethanol precipitated. Ligation was performed by using chromosomal DNA:pBD64 plasmid at a ratio of 1:1 using 2 μg DNA/10 ul and adding 1 unit of T4 ligase and incubating at room temperature (~25° C.) for 60 min. and was terminated by freezing the DNA at −70° C. B. subtilis strain BR151 harboring pUB110 was transformed with the ligated DNA and plated on Luria broth plus 1.1% agar and 3% skim milk, and incubated at 37° C. After sixteen hours, a lawn of transformants was observed on the direct transfer plate. There were approximately 2,000 colonies on the $10^{31\ 1}$ dilution plate and approximately 240 colonies onto the $10^{-2}$ plate. Zones of clearing of the milk were observed after 17 hours and colonies from the cleared zones were picked and streaked for single colonies. After 24 hours the entire plate cleared due to protease produced by the recipient strain. The single colonies were isolated and grown in Penassay broth with 10 ug/ml chloramphenicol for five hours at 37° C.

EXAMPLE II

Isolation and Identification of Plasmids pGX2109, pGX2110 and pGX2111

The culture was centrifuged and the plasmids were isolated from the cell pellet by the boiling preparation method modified as follows. The cells were resuspended in 350 ul of 8% Sucrose, 5% Triton, 50 mM EDTA 50 mM Tris pH 8.0 (STET), 500 ug lysozyme was added, and the suspension was incubated for 15 minutes at 37° C., then boiled for one minute. The chromosomal DNA and the protein were removed by centrifugation at 12,000×G for 20 minutes, and 5 ul proteinase K (50 ug/ml) was added to the pellet and incubated for twenty minutes at 37° C. The sample was heated for twenty minutes at 70° C. to inactivate the proteinase K. Two volumes of isopropyl alcohol were added to precipitate the DNA and the solution was allowed to stand for 30 minutes at −20° C. The pellet was washed with 70% ethyl alcohol and dried in vacuo. The plasmid DNA was dissolved in 50 ul of distilled water and five ul was used to transform B. subtilis (BR151). The transformants were screened for kanamycin and/or chloramphenicol resistance and clearance of milk. Transformed colonies were either kanamycin resistant, chloramphenicol resistant and protease positive or kanamycin resistant, chloramphenicol resistant and protease negative. No protease positive chloramphenicol sensitive colonies were found. Nine independent clones were identified.

The nine clones were single colony purified by streaking onto Luria broth, 1.1% agar and 3% skim milk. The extracellular supernatant from each purified colony was assayed for protease activity in the presence of EDTA or phenylmethylsulfonyl flouride using the procedure of Vasantha and Freese, J. Bact., 144:1119-1125 (1980). The protease activities of two colonies were inhibited by EDTA to 95% and not inhibited by PMSF. Seven were inhibited by PMSF (95%) and not by EDTA. The former were designated as producing neutral protease, the latter as producing alkaline protease.

Figure 1:
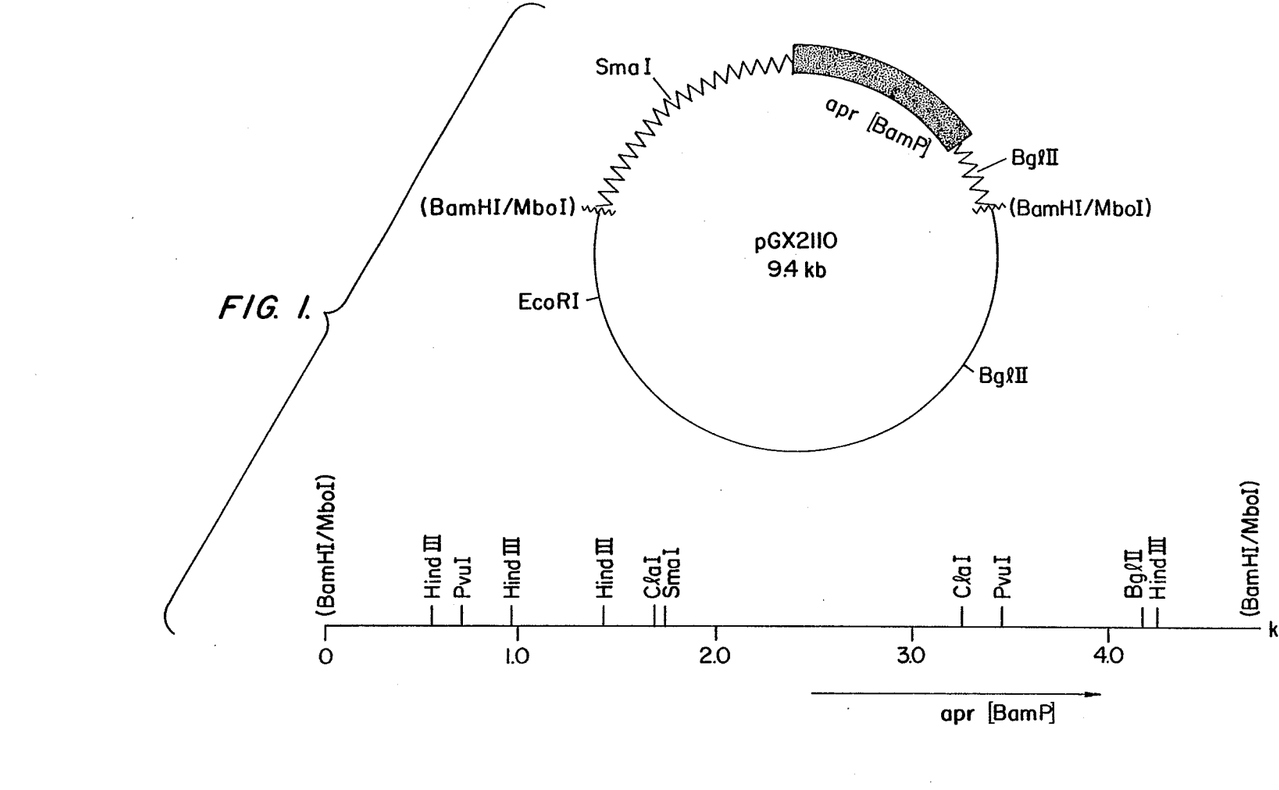
FIG. 1 represents a partial restriction map of the plasmid pGX2110 which was produced by inserting into pBD64 an insert encoding a promoter and regulatory region, as well as the associated structural gene for alkaline protease (apr[BamP]) derived from B. amyloliquefaciens.
Figure 2:
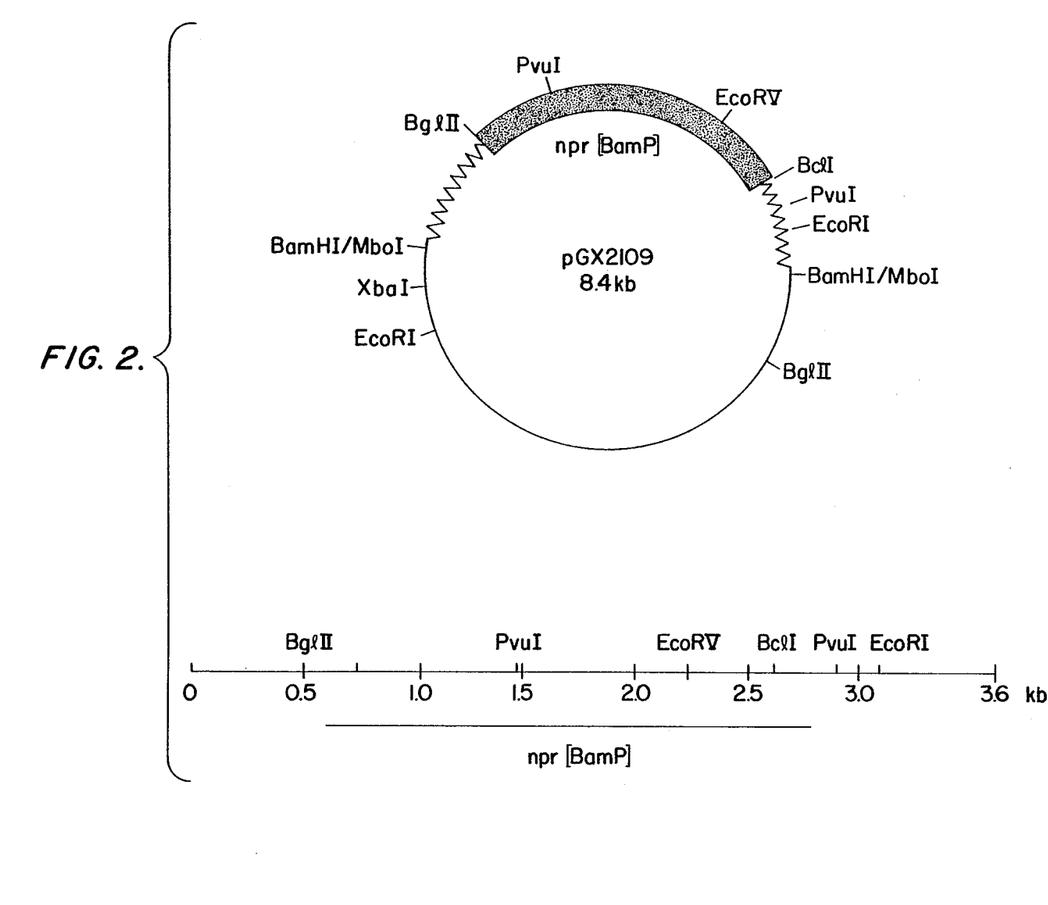
FIG. 2 is a partial restriction map of the plasmid pGX2109 which was produced by inserting into pBD64 an insert encoding a promoter and regulatory region, as well as the associated structural gene for neutral protease (npr[BamP]) derived, from B. amyloliquefaciens.

Plasmids from each single colony were isolated as previously mentioned. The isolated plasmids were restriction mapped. The colonies producing neutral protease contained one plasmid, labelled pGX2109 which has restrictions sites as shown in FIG. 2. It has been deposited at the USDA Northern Regional Research Laboratory, Peoria, Ill. as B15436. The alkaline protease-producing colonies contain two closely related plasmids labelled pGX2110 and pGX2111. Restriction sites in pGX2110 are illustrated in FIG. 1. Plasmid pGX2111 gave an identical restriction map to pGX2110, except that it contained an additional 600 base pair segment in the BglII-BamHI/MboI region at the 3' end of the insert. Plasmid pGX2110 has been deposited at NRRL as B15437.

In order to identify the location of the control region and structural gene in the insert in pGX2110, an eight base pair SalI linker was introduced into various restriction sites to determine its effect on protease production. In separate experiments, the plasmid was either digested with SmaI or HindIII, and BglII and treated with SI nuclease using the conditions suggested by manufacturer. The SalI linker was inserted at the cleavage site using T4 ligase. The plasmid containing the linker was used to transform B. subtilis (Contente and Dubnau, supra). The transformants were assayed for protease activity by their ability to clear skim milk. Introduction of the SalI linker at the SmaI site, the BglII site and HindIII sites did not inactivate the protease gene. The plasmid was then cleaved with ClaI and the large fragment recircularized by ligation in the presence of T4 ligase and used to transform B. subtilis. The transformants assayed negative for protease activity. Based on the results of these experiments, it is clear that the ClaI site is in the gene for apr[Bamp]. The amino acid sequence deduced from the DNA sequence shows extensive homology to the published amino acid sequence of subtilisin (FIG. 3) and the ClaI site was in codon 36 of the mature protein.

EXAMPLE III

Hyperproduction of Protease in B. subtilis Cultures

Plasmids pGX2109 (neutral protease), pGX2110 (alkaline protease) and pBD64 (the plasmid which was used to form the vector for transforming B. subtilis BR151) were used to transform B. subtilis BR151. The transformants as well as B. amyloliquefaciens were grown separately in Penassay broth. Protease activity in the supernatant was measured using hide powder azure as the substrate. B. subtilis transformed by pGX2109 and pGX2110 were essentially equivalent in protease activity after 48 hours and ten-fold more productive of protease than B. amyloliquefaciens. B. subtilis transformed by pBD64 exhibited less than one-tenth of the B. amyloliquefaciens activity and one-one hundredth the activity of B. subtilis transformed by pGX2109 or pGX2110.

EXAMPLE IV

Expression of Protease in Stage Zero Sporulation Mutants of B. subtilis

Protease negative, stage zero sporulation mutants of B. subtilis (strain name IS53,SpOOB,) were transformed by the previously described procedure. Cells were plated on L.B. 1.1% agar and 3% skim milk. Clearance of milk was indistinguishable from pGX2110 in BR151 (a sporulating strain). The replicable plasmidic expression vector is therefore capable of expression in non-protease producing B. subtilis cell lines and in particular, one not normally producing spores. Naturally occuring stage zero sporulating B. subtilis is not found to produce proteases and a correlation is observed between the lack of sporulation and the lack of protease production.

EXAMPLE V

Construction of secretion vectors for Δ22-protein A using apr[BamP] signal sequences Secretion vector using apr[BamP] signal sequence The entire apr[BamP] gene was cloned in the M13 phage vector M13mp9 (Messing and Viera, Gene, 19:269-276 [1982]) as an EcoRI-SalI fragment from the plasmid pGX2125. Plasmid pGX2125 was produced by subcloning a SmaI-BglII fragment from pGX2110, containing apr[BamP], into pGX2104, where it is present on an EcoRI-SalI fragment. Using the oligonucleotide-directed mutagenesis procedure of Norris et al., (Nuc. Acids Res., 11:5103–5112 [1983]), a BamHI site was created just after the junction of the signal coding sequence and the pro sequence by inserting the sequence GGATCC as follows:

M13mp9 containing apr[BamP] was grown in YT broth and the single stranded phage DNA was prepared according to Zoller and Smith (supra). The mutagenic oligonucleotide 5'TGCCCAGGCGGCAGG-GGATCCGAAATCAAACGGGGA 3' and the M13mp9 universal primer 5'GTAAAACGACGG-CCAGT 3' were annealed at 20 pmoles and 16 pmoles, respectively to the template DNA (0.8 to 1.0 pmole). Annealing and elongation were carried out according to Norris et al. After 2 hours incubation at room temperature, the mutagenic mix was digested with EcoRI and SalI and ethanol precipitated using EcoRI and SalI digested pGX251 (shuttle vector) as carrier DNA. An aliquot of the precipitated DNA was subject to gel electrophoresis to verify that the fragment of interest (EcoRI to SalI fragment) had been successfully synthesized in vitro. The rest of the precipitated DNA was ligated and E. coli was transformed with the ligated DNA. 24 of the E. coli transformants were screened for the presence of the BamHI site and one was found to contain the BamHI site. That plasmid has been designated as pGX2134 (see FIG. 5), which is capable of replication in both E. coli and B. subtilis. Plasmid pGX2134 can be used for insertion of any heterologous gene having a BamHI-compatible site at its 5' end and to direct expression and secretion of the heterologous gene product in B. subtilis.

Figure 5:
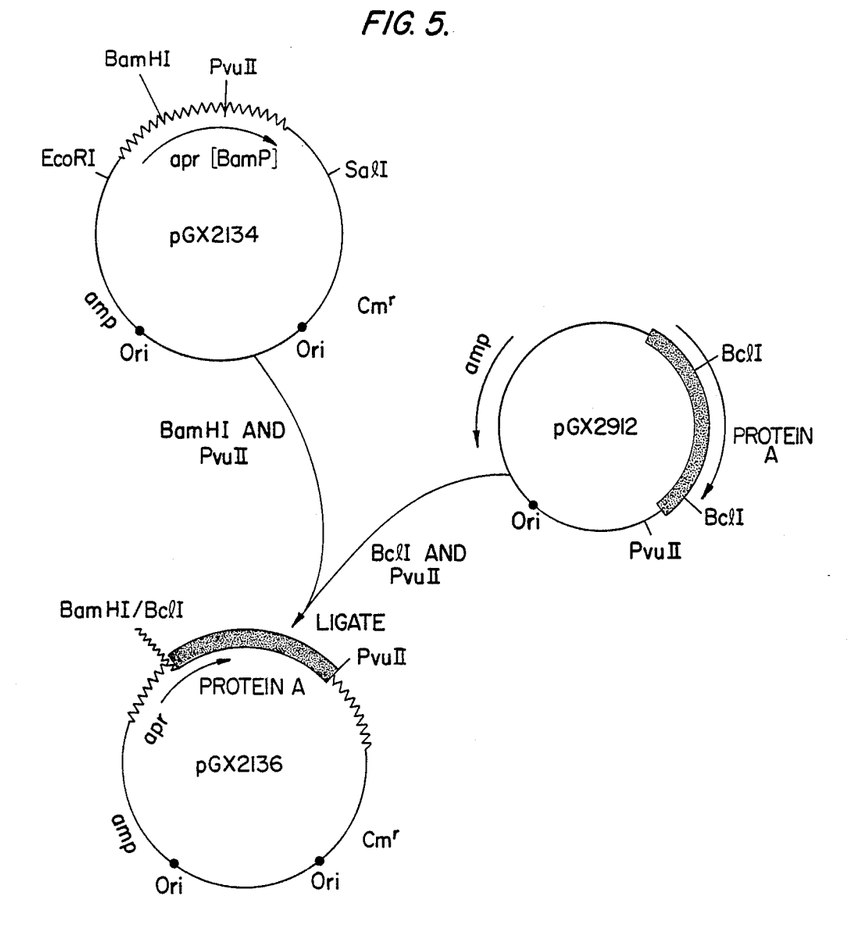
FIG. 5 is a graphic illustration of the construction of plasmid pGX2136 which contains a portion of the gene coding for protein A (S. aureus) fused in-frame to the 3' end of the signal sequence of apr[BamP].

Plasmid pGX2912 contains a full-length gene coding for protein A from S. aureus (see FIG. 5). Plasmid pGX2912 was digested (partially) with BclI and with PvuII. The BclI-PvuII fragment contained the entire 3' end of the protein A gene beginning with the codon for amino acid 23 (Δ22-protein A). The BclI sticky end is complementary with the sticky end produced by BamHI cleavage.

Plasmid pGX2134 was digested with BamHI and PvuII. The BclI-PvuII fragment coding for Δ22-protein A was ligated to cleaved pGX2134 DNA to produce plasmid pGX2136 (see FIG. 5). Plasmid pGX2136 contains the promoter and regulatory regions of apr-[BamP], including the signal peptide coding sequence, fused to the Δ22-protein A gene through two codons, GCA GGG, corresponding to the first two amino acids of the pro-region from apr[BamP]. The sequence of pGX2136 at the fusion of the apr[BamP] and Δ22-protein A coding sequences can be illustrated as follows:

Secretion vector using npr[BamP] signal sequence

Figure 6:
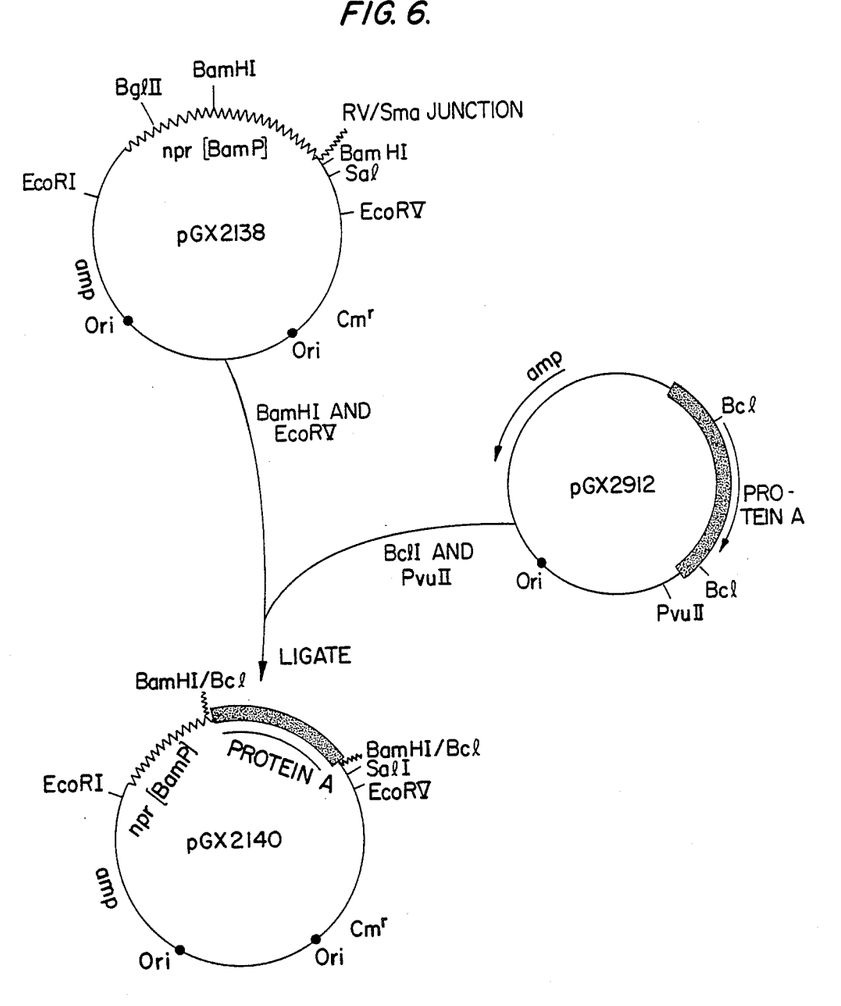
FIG. 6 is a graphic representation of the construction of plasmid pGX2140 which contains a portion of the gene coding for protein A (S. aureus) fused in-frame to the 3' end of the signal sequence of npr [BamP].

An EcoRI-EcoRV fragment from the plasmid pGX2109 containing a portion of the npr[BamP] gene coding for the promoter, signal sequence, pro-region and approximately 60% of the mature protein was cloned in the M13 phage vector M13mp19 (J. Norrander, T. Kempe and J. Messing, *Gene*, 26:101-106 [1983]) at the EcoRI and SmaI site. M13mp19 containing the npr[BamP] (EcoRI to EcoRV) fragment was highly unstable. Therefore, independent plaques (~36) were screened for the phage with the entire insert by agarose gel electrophoresis. Single stranded DNA was made from these and oligonucleotide directed mutagenesis was performed using the method of Norris et al., as follows:

The mutagenic oligonucleotide 5'TGTTCAGGCCGCTCAGGATCCGAATCCT-CAGCTTAA 3' (20 pmoles) and the M13 universal primer (12 pmoles) were used with template DNA (0.8 to 1.0 pmoles). The mutagenesis was performed as outlined for apr[BamP]. *E. coli* was transformed and 24 transformants were screened and one had the BamHI site and that plasmid was designated as pGX2138 (see FIG. 6), which is capable of replication in both *E. coli* and *B. subtilis*. Plasmid pGX2138 can be used for insertion of any heterologous gene having a BamHI-compatible site at its 5' end to direct expression and secretion of the heterologous gene product in *B. sutilis*.

Plasmid pGX2138 was digested with BamHI and EcoRV. Plasmid pGX2912, containing the protein A gene, was digested (partially) with BclI and with PvuII. The BclIPvuII fragment coding for Δ22-protein A was ligated to the cleaved pGX2138 DNA (EcoRV and PvuII cleavage both generate blunt ends) to produce plasmid pGX2140 (see FIG. 6). Plasmid pGX2140 contains the promoter and regulatory regions of npr[BamP], including the signal peptide coding sequence, as well as two codons, GCT GAG, corresponding to the first two amino acids of the pro-region of npr[BamP]. Restriction analysis of pGX2140 indicated that it had picked up the entire BclI fragment of the protein A gene missing the 22 amino acids at the N-terminus and 45 amino acids at the C-terminus. The sequence of pGX2140 at the junction of the npr[BamP] and Δ22-protein A coding sequences is similar to that illustrated above for the apr[BamP]/Δ22-protein A fusion with the two amino acids being ala and glu at the junction.

EXAMPLE VI

Expression and secretion of Δ22-protein A

Plasmids pGX2136, containing a α22-protein A coding sequence under the control of the apr[BamP] promoter and regulatory region, and pGX2140, containing a Δ22-protein A (less 45 C-terminal amino acids) coding sequence under the control of the npr[BamP] promoter and regulatory region, were each used to transform *B. subtilis* strain 4935 by the procedure of Chang and Cohen (Mol. gen. Genet., 168:111-115 [1979]) and transformants were selected for chloramkphenicol resistance. *B. subtilis* strain 4935 is a low protease derivative strain of *B. subtilis* BR151. All the chloramphenicol resistant transformants were found to be protein A positive by enzyme-linked immunosorbent assay.

Transformants carrying pGX2136 and pGX2140 were each inoculated into two different culture media (see Table I) and grown for 24 hours. The amount of Δ22-protein A secreted into the medium was determined by the procedure of Lofdhal et al. (*Proc. Nat,l. Acad. Sci.*, 80:697-701. Results are presented in Table I. The results show that the promotor and regulatory regions of both the apr[BamP] and npr[BamP] genes were capable of directing expression and secretion of a heterologous protein in *B. subtilis*.

TABLE I

| Medium | Amount of Secreted Protein A (mg/l) | |
|---|---|---|
| | pGX2136 in GX4935 | pGX2140 in GX4935 |
| Medium A[1] | 3 | 710 |
| Synthetic medium[2] | 10 | 60 |

[1]Medium A contains (per liter): Tryptone 33 g; Yeast extract 20 g; NaCl 7.4 g; 3 M NaOH 12 ml; Na$_2$HPO$_4$ 8 g; KH$_2$PO$_4$ 4 g; Casamino acids 20 g; Glucose 10 g; MnCl$_2$ 0.06 mM, and Initial pH 7.5.
[2]Synthetic medium as described by Vasantha and Freese, J. Bacteriol., 144:1119-1125 (1980) with 100 mM MOPS replaced by 100 mM potassium phosphate + 1% glucose + 0.2% malate + 1% yeast extract + 1% casamino acids.

EXAMPLE VII

Construction of secretion vectors for prorennin using apr[BamP] and npr signal sequences

*E. coli* strain GX1670 contains plasmid pGX2231, which carries a gene coding for a fusion of the first 27 amino acids of the trpB expression product and the sequence of prorennin, less its 2 N-terminal amino acids Δ2-prorennin), linked through a 10-amino acid spacer sequence. Δ2-Prorennin has been shown to have the biological activity of full-length prorennin, i.e., it is capable of undergoing autocatalytic cleavage to produce the active form of the milk clotting enzyme rennin (see copending commonly assigned U.S. patent application Ser. No. 528,421, the disclosure of which is incorporated by reference). Strain GX1670 has been deposited at the USDA Northern Regional Research Laboratory, Peoria, Illinois, with accession number NRRL B-15571.

Plasmid pGX2231 is extracted from *E. coli* strain GX1670 by the method of Holmes and Quigley (*Anal. Biochem.*, 114:193-197 ([1981]). Using the procedure of Norris et al., supra, a BclI restriction site is introduced just upstream of the 2-prorennin coding region by inserting the hexanucleotide TGA TCA as follows:

```
                    BclI
              ┌───────────┐
...TTC GAC CAT GAT CAG ATC ACC AGG...
       asp   gln  ile  thr  arg
```

The Δ2-prorennin gene containing the synthesized BclI site is cleaved with BclI and with any restriction enzyme which generates a blunt end 3' to the transcription terminator of the gene.

Plasmid pGX2134 (Example V), containing the apr-[BamP] gene with the BamHI site inserted just downstream from the signal peptide coding sequence, is digested with BamHI and PvuII and the small fragment is discarded. The large fragment from cleaved pGX2134 is ligated to the BclI digested Δ2-prorennin gene. The resultant plasmid contains the complete apr[BamP] signal peptide coding region linked in-frame to the coding region for Δ2-prorennin through a sequence encoding -ala-gly-asp-gln-.

Plasmid pGX2138 (Example V), containing the npr[BamP]gene with the BamHI site inserted just downstream from the signal peptide coding sequence, is digested with BamHI and EcoRV and the small fragment is discarded. The large fragment from pGX2138 is ligated to the BclI digested Δ2-prorennin gene produced as described above. The resultant plasmid contains the complete nr[BamP] signal peptide coding region linked in-frame to the coding region for Δb 2- 0 prorennin through a sequence encoding -ala-glu-asp-gln-.

Each of the plasmids containing the apr[BamP]/Δb 2-prorennin and npr[BamP]/Δb 2-prorennin fusions is used to transform B. subtilis strain BR151 by the procedure of Chang and Cohen, supra, and transformants are selected for chloramphenicol resistance. Chloramphenicol resistant transformants are inoculated into culture media and grown overnight. The presence of secreted proteins containing the Δb 2-prorennin sequence is confirmed by Western blot analysis. The secreted protein, which can be recovered from the medium by conventional procedures, is capable of being autocatalytically cleaved to produce active rennin by the procedure of U.S. patent application Ser. No. 528,421.

EXAMPLE VIII

Expression and Secretion of Alkaline Protease During Post-Exporential Growth of B. subtilis A transformant strain of B. subtilis carrying the apr [BamP] gene on a multicopy plasmid was prepared by transforming B. subtilis strain GX4935 (low protease derivative of strain BR151) with plasmids pGX2110 and pBD64 using procedures previously described. The resulting transformant strain, identified as GX2821, was grown on a synthetic culture medium (Vasantha et al., J. Bact., 159, 811-819 [1984]) supplemented with 0.1% yeast extract. Cell density ($A_{600}$) was monitored and the growth medium was periodically assayed for protease activity by a procedure similiar to that described by Geele, G. et al. in "Spores", Vol., p. 391-396, Eds. Gerhardt, B. et al., American Society of Microbiology (1975). The assay measured color development as a result of proteolysis of azocasein at pH 8.0. Units of activity are defined as $\Delta A_{420}$ per ml. per hr. at 37° C.

Cell density and extracellular protease activity were plotted vs. time of fermentation. The results are presented in FIG. 7. Very little alkaline protease production occurred during exponential growth whereas a large increase was observed after the end of exponential growth. Analysis of the culture supernatant is SDS-polyacrylamide gel showed an increase in the amount of extracellular alkaline protease paralleling the increase in enzyme activity. Similar results were obtained when GX2821 was grown in complex media (Penassay broth, brain heart infusion broth, nutrient sporulation medium).

A B. subtilis strain, GX4935, which was transformed with pGX2136 (see Example V), containing the Δ22 protein A coding sequence linked to the promoter and regulatory region of apr[BamP] grown on Medium A (see Example VI) and was observed to accumulate Δ22 protein A during the postexponential growth phase in a manner similar to that shown in FIG. 7 for alkaline protease.

The marked growth phase dependency of alkaline protease expression indicates that a heterologous gene can be linked to the promoter and regulatory region of apr [BamP] in order to obtain the bulk of production of the heterologous protein during the post-exponential growth phase.

EXAMPLE IX

Expression and Secretion of Neutral Protease During Exponential Growth of B. subtilis A transformant strain of B. subtilis carrying the npr [BamP] gene on a multicopy plasmid was prepared by transforming B. subtilis strain GX4935 with plasmid pGX2109 using procedures previously described. The resulting transformant strain, identified as GX2842, was grown on synthetic culture medium (Vasantha et al., J. Bact., 15, pp. 811-819 [1984]) supplemented with 0.1% yeast extract. Cell density was monitored and the growth medium was periodically assayed for protease activity on the azocasein substrate (see Example VIII) at pH 7.0.

Cell density and extracellular protease activity were plotted vs. time of fermentation. The results are presented in FIG. 8. Protease activity showed a substantial increase during exponential growth as well as an additional increase after the end of exponential growth. The increase in enzyme activity corresponded to an increase in the amount of extracellular neutral protease in the growth medium, determined by SDS-gel electrophoresis. Similar results were obtained when GX2842 was grown in complex media (Penassay broth, brain heart infusion broth, nutrient sporulation medium).

A B. subtilis strain, GX4935, which was transformed with pGX2140 (see Example V), containing the coding sequence for Δ22 protein A (less 45 C-terminal amino acids) linked to the promoter and regulatory region of npr[BamP] was grown on Medium A (see Example VI) and was observed to accumulate Δ22 protein A during the exponential growth phase in a manner similar to that shown in FIG. 8 for neutral protease.

The marked growth phase dependecy of neutral protease activity indicates that a heterologous gene can be linked to the promoter and regulatory region of npr[BamP] in order to obtain production of the heterologous protein during exponential growth.

What we claim is:

1. A process for producing a microorganism for the expression of a protease enzyme which comprises transforming calls of a first Bacillus species with a replicable plasmidic expression vector comprising:
    (a) a replicon;

(b) a DNA sequence comprising the promoter and regulatory regions which control expression and secretion of a protease in cells of a second Bacillus species; and
(c) a DNA sequence encoding the amino acid sequence of the desired protease, operably linked to said promoter and regulatory regions.

2. A process as claimed in claim 1, wherein the Bacillus which is transformed is a *B. subtilis* and the DNA sequences encoding the promoter and regulatory regions and the protease are *B. amyloliquefaciens* sequences.

3. A process as claimed in claim 2, wherein the *B. amyloliquefaciens* protease is selected from the group consisting of neutral protease and alkaline protease.

4. A process as claimed in claim 2, wherein said *B. amyloliquefaciens* protease is a neutral protease.

5. A process as claimed in claim 2, wherein said *B. amyloliqufaciens* protease is an alkaline protease.

6. A process as claimed in claim 2, 3, 4 or 5 wherein said *B. subtilis* contains a homologous plasmid having sufficient DNA sequence homology to sequences in said replicable plasmidic expression vector, whereby homologous recombination is capable between said homologous plasmid and said expression vector.

7. A replicable plasmidic expression vector capable of directing high level expression and secretion of a polypeptide in cells of a transformed Bacillus species which comprises:
(a) a replicon;
(b) a DNA sequence comprising the promoter and regulatory regions which control expression and secretion of a Bacillus protease and wherein said DNA sequence is heterologous to and operable in said transformed Bacillus species; and
(c) a DNA sequence encoding the amino acid sequence of a polypeptide, operably linked to said promoter and regulatory regions.

8. A replicable plasmidic expression vector as claimed in claim 7, wherein the DNA sequence comprising the promoter and regulatory regions is a sequence which controls the expression and secretion of a *B. amyloliquefaciens* protease.

9. A replicable plasmidic expression vector as claimed in claim 8, wherein said polypeptide is a *B. amyloliquefaciens* protease.

10. A replicable plasmidic expression vector as claimed in claim 8, wherein said polypeptide is a *B. amyloliquefaciens* neutral protease.

11. A replicable plasmidic expression vector as claimed in claim 8, wherein said polypeptide is a *B. amyloliquefaciens* alkaline protease.

12. The plasmid pGX2109.
13. The plasmid pGX2110.
14. The plasmid pGX2111.

15. A microorganism which has been transformed with the replicable plasmidic expression vector of claim 7.

16. A microorganism which has been transformed with the replicable plasmidic expression vector of claims 8, 9, 10 or 11.

17. A microorganism of a Bacillus species which has been transformed by the plasmid pGX2109.

18. A microorganism of a Bacillus species which has been transformed by the plasmid pGX2110.

19. A microorganism of a Bacillus species which has been transformed by the plasmid pGX2111.

20. A microorganism as claimed in claims 15, 17, 18 or 19 wherein said microorganism is *B. subtilis*.

21. A microorganism as claimed in claim 16 wherein said microorganism is a *B. subtilis*.

22. A mehod of producing a polypeptide which comprises:
(a) transforming cells of a first Bacillus species with a replicable plasmidic expression vector comprising:
(i) a replicon; p2 (ii) a DNA sequence comprising the promoter and regulatory regions which control expression and secretion of a protease in cells of a second Bacillus species; and
(iii) a DNA sequence encoding the amino acid sequence of a polypeptide heterolgous to and operably linked to said promoter and regulatory regions;
(b) growing the transformed cells of a first Bacillus species in a culture medium and subjecting said transformed cells to conditions under which the polypeptide is expressed and secreted into the medium; and
(c) recovering the polypeptide from the medium.

23. A method as claimed in claim 22, wherein the promoter and regulatory regions control expression of a protease in *B. amyloliquefaciens*.

24. A method as claimed in claim 23 wherein the Bacillus which is transformed is a *B. subtilis*.

25. A method as claimed in claim 24 wherein said polypeptide is a *B. amyloliquefaciens* protease.

26. A method as claimed in claim 24 wherein said polypeptide is a *B. amyloliquefaciens* neutral protease.

27. A method as claimed in claim 24 wherein said polypeptide is a *B. amyloliquefaciens* alkaline protease.

28. A method as claimed in claim 24 wherein said replicable plasmidic expression vector is the plasmid pGX2109.

29. A method as claimed in claim 24 wherein said replicable plasmidic expression vector is the plasmid pGX2110.

30. A method as claimed in claim 24 wherein said replicable plasmidic expression vector is the plasmid pGX2111.

31. A replicable plasmidic expression and secretion vector comprising the promotor and regulatory regions of a gene selected from the group consisting of the alkaline protease gene and neutral protease gene from *B. amyloliquefaciens* strain P and wherein said gene having fused, inframe, to the 3' end of the signal peptide coding sequence thereof, a structural gene encoding a polypeptide other than a *B. amyloliquefaciens* protease.

32. A replicable plasmidic expression and secretion vector as claimed in claim 31, wherein the structural gene which is fused to the promotor and regulatory region contains at least a portion of the prorennin gene sequence and wherein said gene sequence encodes a polypeptide having prorennin activity.

33. A replicable plasmidic expression and secretion vector as claimed in claim 32, wherein the protein containing at least a portion of the prorennin gene sequence is delta 2-prorennin.

34. A replicable plasmidic expression and secretion vector as claimed in claim 31, wherein the structural gene which is fused to the promotor and regulatory region contains at least a portion of the protein A gene sequence and wherein said gene sequence encodes a polypeptide having protein A activity.

35. A replicable plasmidic expression and secretion vector as claimed in claim 34, wherein the protein containing at least a portion of the protein A gene sequence is delta 22-protein A.

36. A microorganism of the genus and species Bacillus subtilis which has been transformed with the replicable plasmidic expression and secretion vector of claims 31, 32, 33, 34 or 35.

37. An expression and secretion vector comprising a replicable plasmid containing the promoter and regulatory regions of a gene selected from the group consisting of the alkaline protease gene and neutral protease gene from *B. amyloliquefaciens* strain P and a sequence of deoxyribonucleotides, adjacent the 3' end of the signal peptide coding sequence, which comprises an endonuclease restriction site not naturally present in the alkaline or neutral protease genes from *B. amyloliquefaciens* strain P.

38. A vector as claimed in claim 37, wherein the promoter and regulatory regions are from the alkaline protease gene from *B. amyloliquefaciens*.

39. A vector as claimed in claim 38, wherein the endonuclease restriction site adjacent the 3' end of the signal peptide coding sequence is a BamHI site.

40. Plasmid pGX2134.

41. A vector as claimed in claim 37, wherein the promoter and regulatory regions are from the neutral protease genes from *B. amyloliquefaciens*.

42. A vector as claimed in claim 41, wherein the endonuclease restriction site adjacent the 3' end of the signal peptide coding sequence is a BamHI site.

43. Plasmid pGX2138.

44. A method of producing a polypeptide which comprises:
 (a) transforming cells of a first Bacillus species with a replicable plasmidic expression vector comprising:
  (i) a replicon;
  (ii) a DNA sequence comprising the promoter and regulatory regions which control, expression and secretion of neutral protease in cells of a first Bacillus species; and
  (iii) a DNA sequence encoding the amino acid sequence of a polypeptide heterologous to and operably linked to said promoter and regulatory regions;
 (b) growing the transformed cells of a first Bacillus species in culture medium; and
 (c) expressing the heterologous polypeptide during exponential growth of said transformed cells.

45. A method as claimed in claim 44, wherein the promoter and regulator regions are the promoter and regulatory regions of the neutral protease genes from *B. amyloliquefaciens*.

46. A method of producing a polypeptide which comprises:
 (a) transforming a bacillus with a replicable plasmidic expression and secretion vector comprising:
  (i) a replicon;
  (ii) a DNA sequence comprising the promoter and regulatory regions which control expression and secretion of alkaline protease cells of a first Bacillus species; and
  (iii) a DNA sequence encoding the amino acid sequence of a polypeptide heterologous to and operably linked to said promoter and regulatory regions;
 (b) growing said transformed cell in a culture medium; and
 (c) expressing the heterologous polypeptide after exponential growth of said transformed cells has ceased.

47. A method as claimed in claim 46, wherein the promoter and regulatory regions are the promoter and regulatory regions of the alkaline protease genes from *B. amyloliquefaciens*.

* * * * *